US012697166B2

(12) United States Patent
Collins

(10) Patent No.: US 12,697,166 B2
(45) Date of Patent: Aug. 4, 2026

(54) APPARATUS, SYSTEMS, AND METHODS FOR IDENTIFYING INSTRUMENTS IN LAPAROSCOPIC AND OTHER MINIMALLY INVASIVE SURGERY

(71) Applicant: John Craig Collins, Long Beach, CA (US)

(72) Inventor: John Craig Collins, Long Beach, CA (US)

( * ) Notice: Subject to any disclaimer, the term of this patent is extended or adjusted under 35 U.S.C. 154(b) by 484 days.

(21) Appl. No.: 16/512,183

(22) Filed: Jul. 15, 2019

(65) Prior Publication Data

US 2019/0336203 A1     Nov. 7, 2019

Related U.S. Application Data

(62) Division of application No. 14/020,875, filed on Sep. 8, 2013, now Pat. No. 10,350,001.

(60) Provisional application No. 61/698,599, filed on Sep. 8, 2012.

(51) Int. Cl.
| | |
|---|---|
| *A61B 18/14* | (2006.01) |
| *A61B 34/30* | (2016.01) |
| *A61B 90/90* | (2016.01) |
| *A61B 90/92* | (2016.01) |
| *A61B 90/94* | (2016.01) |

(52) U.S. Cl.
CPC .......... *A61B 18/1482* (2013.01); *A61B 90/90* (2016.02); *A61B 90/92* (2016.02); *A61B 90/94* (2016.02); *A61B 18/1445* (2013.01); *A61B 34/30* (2016.02)

(58) Field of Classification Search
CPC . A61B 18/1482; A61B 18/1445; A61B 90/90; A61B 90/92; A61B 90/94; A61B 34/30
See application file for complete search history.

(56) References Cited

U.S. PATENT DOCUMENTS

| | | | | | |
|---|---|---|---|---|---|
| 5,190,541 | A | * | 3/1993 | Abele | ................ A61B 18/1442 |
| | | | | | 606/49 |
| 6,783,524 | B2 | * | 8/2004 | Anderson | .............. A61B 34/37 |
| | | | | | 606/1 |
| 2003/0163219 | A1 | * | 8/2003 | Flesher | ................ G09B 19/003 |
| | | | | | 700/185 |
| 2006/0186210 | A1 | * | 8/2006 | Tethrake | .............. G06K 19/005 |
| | | | | | 235/492 |

(Continued)

*Primary Examiner* — William J Levicky
*Assistant Examiner* — Jessandra F Hough
(74) *Attorney, Agent, or Firm* — William A. English; Vista IP Law Group LLP

(57) ABSTRACT

Systems and methods are provided for identifying surgical instruments, e.g., MIS instruments, including a shaft including a proximal end and a distal end sized for introduction into a patient's body, a tool tip on the distal end including an end effector, and a handpiece or connector on the proximal end. One or more identifier members may be provided on the proximal end and/or distal end of the shaft, on the handpiece, and/or on the tool tip to identify one of a type and a class of the end effector. For example, a set of surgical instruments may be provided that include identifier knobs added onto the shafts to identify different tool tips, the shafts may include different outer shapes and/or textures, or colored and/or luminescent features may be provided on the instruments.

25 Claims, 3 Drawing Sheets

(56)  References Cited

U.S. PATENT DOCUMENTS

| | | | |
|---|---|---|---|
| 2007/0263375 A1* | 11/2007 | Birkenbach ............ | A61B 90/39 |
| | | | 362/34 |
| 2008/0243088 A1* | 10/2008 | Evans .................... | A61B 90/98 |
| | | | 604/246 |
| 2009/0317002 A1* | 12/2009 | Dein ....................... | A61B 50/36 |
| | | | 382/224 |
| 2013/0253480 A1* | 9/2013 | Kimball .................. | H04L 67/32 |
| | | | 606/1 |
| 2014/0074134 A1* | 3/2014 | Skarbnik ................ | A61B 90/90 |
| | | | 606/170 |

* cited by examiner

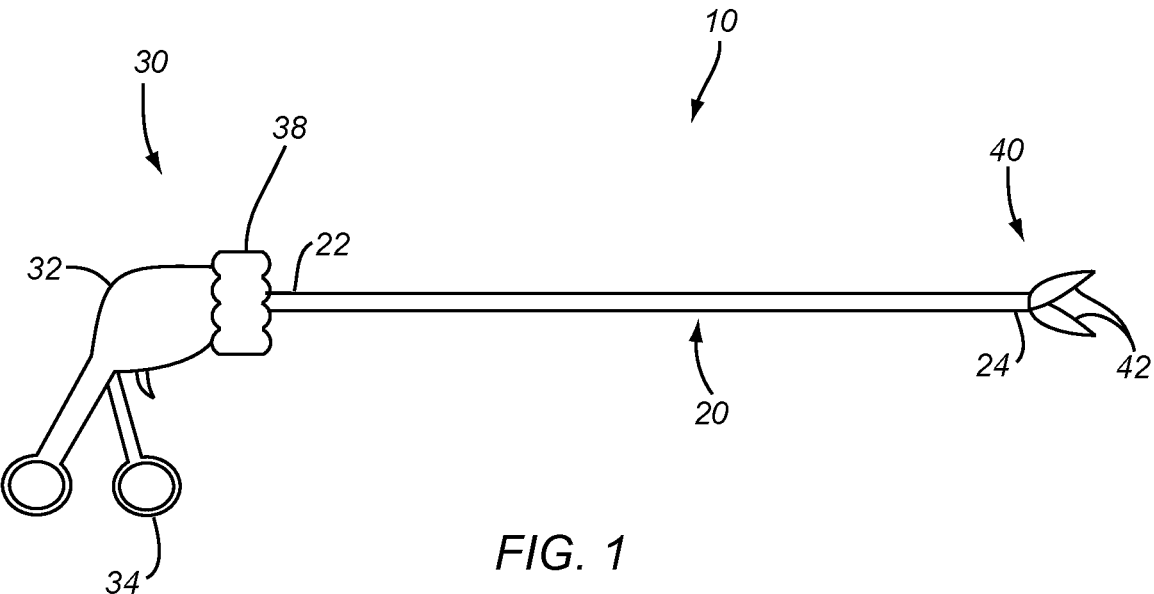
FIG. 1
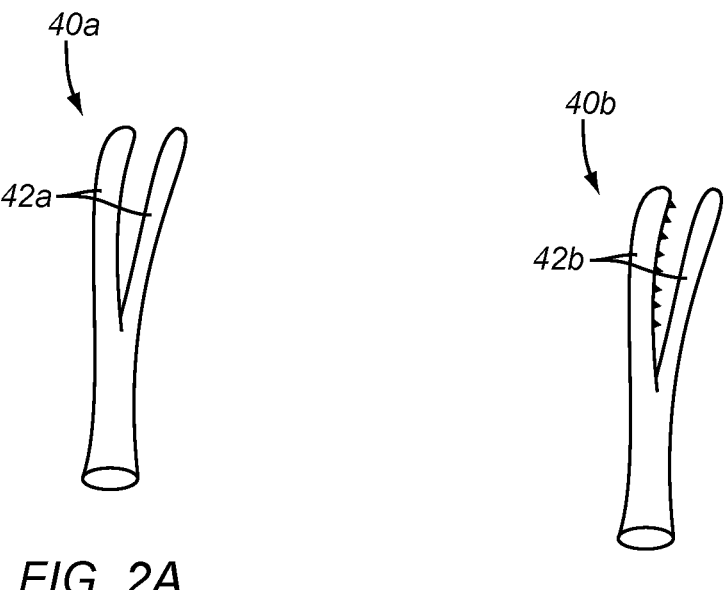
FIG. 2A
FIG. 2B

APPARATUS, SYSTEMS, AND METHODS FOR IDENTIFYING INSTRUMENTS IN LAPAROSCOPIC AND OTHER MINIMALLY INVASIVE SURGERY

RELATED APPLICATION DATA

This application is a divisional of co-pending application Ser. No. 14/020,875, filed Sep. 8, 2013, issuing as U.S. Pat. No. 10,350,001, which claims benefit of U.S. provisional application Ser. No. 61/698,599, filed Sep. 8, 2012, the entire disclosures of which are expressly incorporated by reference herein.

FIELD OF THE INVENTION

The present invention relates generally to apparatus, systems, and methods for identifying instruments used in surgery, e.g., laparoscopic or other minimally-invasive surgery, and more particularly, to apparatus, systems, and methods for confirming to a surgeon and/or other medical personnel during laparoscopic, thoracoscopic, robotic, or other minimally-invasive surgery that certain instruments are in use, and to systems and methods including such identification.

BACKGROUND

Surgery has become progressively less invasive due to advances in medical technology. Laparoscopy is the dominant minimally invasive surgical ("MIS") approach used today and has replaced many traditional "open" approaches. In laparoscopic surgery, tubular members or "trocars" (typically three to five (3-5)) are placed at separate points in the surgical field, e.g., from the patient's skin through intervening tissue to a body cavity or other surgical space (such as the abdomen) within a patient's body. These trocars serve as ports providing access into the surgical space through which specially configured, e.g. long and thin, instruments may be inserted. Manipulation of these instruments from outside the body mechanically translates into motion of tool tips within the body cavity. Depending on the tool tip, different instruments may be used for different functions, such as grasping, blunt dissection, cutting, electrosurgical dissection, clipping, ligating, suturing, or a combination of these. The appropriate instruments may be selected by the surgeon based on what the surgeon needs for individual steps of a particular procedure.

Minimally Invasive Surgery (MIS) offers several advantages compared to open surgical procedures including minimal trauma to the abdominal wall and hence less postoperative pain to the patient, fewer wound complications, earlier patient mobilization, and/or shorter lengths of stay. Laparoscopic access to the peritoneal or pre-peritoneal space is the dominant MIS approach when performing minimally invasive abdominal operations, e.g., cholecystectomy, appendectomy, bowel resection, hernia repair, and the like. Similarly, thoracoscopy may be employed for procedures in the chest cavity. Robotic techniques may incorporate aspects of MIS with the addition of a robotic console and effectors. These operations are technically challenging and require intense concentration on the part of the surgeon and support team.

Laparoscopic and other MIS procedures are typically performed in darkened conditions to facilitate viewing of the operative field, e.g., on a television monitor or other display. For example, the surgeon may place a laparoscope or other instrument through a trocar or port to view the surgical field including the tool tips and tissue structures therein, and the images may be presented on the display. A nurse or technician may pass instruments to the surgeon, as requested, during the course of the procedure. Typically, the surgeon uses two instruments at a time (e.g., one for each hand) and changes the instruments numerous times as the operation proceeds.

Most laparoscopic instruments have a nominal outer diameter or cross-section (including the shaft and tool tip) of less than about five millimeters (5 mm), with some specialized instruments having different diameters, e.g., less than about three millimeters (3 mm), ten millimeters (10 mm), twelve millimeters (12 mm), and the like. However, the types of tool tips on instruments generally used in laparoscopic procedures may be difficult to distinguish from one another even under conditions of good lighting, and thus pose a risk of employing an inappropriate instrument during such procedures.

Instruments from a given manufacturer or product line tend to be substantially identical within the product line. For example, all of the instruments in a set of instruments may have similar diameters and/or shapes, e.g., having the same color and shape of shaft, body, knob, handgrip, locking mechanism, and/or other features, as the other instruments in the set even though they may have different tips and/or functions. Typically, lettering or labeling visible on the instrument, if any, may refer to the name of the manufacturer and not to the function of the instrument. Instruments of a given product line and diameter may generally differ only in the tool tip.

Thus, for example, an instrument with a scissor tip may readily be confused with an instrument with a curved dissector tip during a procedure, with potentially harmful consequences for the patient and/or the medical personnel.

SUMMARY

The present invention relates generally to apparatus, systems, and methods for identifying instruments used in surgery, e.g., laparoscopic or other minimally-invasive surgery. More particularly, apparatus, systems, and methods may be provided for confirming to a surgeon and/or other medical personnel during laparoscopic surgery that certain instruments are in use.

The apparatus, systems, and methods herein may enhance identification of instruments used in surgery, e.g., laparoscopic or minimally invasive surgery including laparoscopy, laparoscopic-assisted, thoracoscopic or "video-assisted thoracic surgery" (VATS), hysteroscopy, robotic surgery, and/or other forms of endoscopic surgery hereafter referred to collectively as MIS. More particularly, the apparatus, systems, and methods herein may include endoscopic instruments including one or more of a color, texture, shape, geometric profile, luminosity, and the like, designed to facilitate the immediate and unequivocal identification of individual instruments.

For example, in one embodiment, at the time of manufacture, the tip, shaft, body, handgrip, and/or knob of each type of instrument (e.g., scissors, graspers, dissectors, coagulators, needle holders, and the like) may be constructed with a tip-specific shape and/or geometric profile and/or color and/or texture and/or luminosity that facilitates unequivocal tactile and/or visual confirmation of the type of instrument. Optionally, the name of the type of instrument or a standardized and/or generally-understood alphanumeric abbreviation, code, or symbol, which corresponds to the type or class of instrument, may be engrossed or otherwise applied on the instrument's body or shaft by the manufacturer.

In accordance with another embodiment, an aftermarket apparatus is provided for modifying existing instruments with distinctive add-on identifier knobs and/or other accessories having differing shape profiles (e.g., round, octagonal, hexagonal, square, triangular, and the like). Such knobs or add-on accessories may be designed from suitable material, such as synthetic rubber or plastic, and may be provided with a hole or aperture that enables the user to slide or otherwise secure a specific identifier accessory over the tip and/or shaft of each instrument to reside flush with the knob or body of the handpiece, thus providing immediate tactile and/or visual confirmation that a particular instrument is selected. The surface texture or consistency may also vary to facilitate tactile discrimination among instrument types or classes. Identifier knobs or features may further be distinguished by instrument-specific color or luminosity to provide additional visual cues. Identifier knobs may be provided in sterile single-use packages or, where feasible and permitted, may be re-sterilized for repeated use.

In accordance with another embodiment, a luminous indicator may be provided having a specific color installed at the time of manufacture to identify each type or class of MIS instruments. For example, a light-emitting diode or other light may be placed in the body or other accessible part of the instrument whose color corresponds to the function of the tool tip. In an exemplary embodiment, a first color may be provided for instruments having a "sharp" tool tip, and second color may be provided for instruments having a "blunt" or substantially atraumatic tool tip. For example, red for scissors and other cutting tips and green for graspers and other blunt tips may be a natural and easily understood system for distinguishing classes of instruments; optionally, other colors may represent yet other types or classes of instruments.

In accordance with yet another embodiment, a surgical instrument is provided that includes a shaft including a proximal end and a distal end sized for introduction into a patient's body; a tool tip on the distal end including an end effector; a handpiece or connector for coupling to a robotic control system on the proximal end; and an identifier member removably secured to the proximal end of the shaft or the handpiece to identify one of a type and a class of the end effector.

In accordance with still another embodiment, a system is provided for performing a surgical procedure that includes a plurality of surgical instruments, each instrument comprising a shaft including a proximal end and a distal end sized for introduction into a patient's body, a tool tip on the distal end including an end effector, and a handpiece or connector for coupling to a robotic control system on the proximal end; and a plurality of identifier members removably secured to the proximal ends of the shafts or the handpieces of respective instruments, the identifier members configured to identify one of a type and a class of the end effectors on the respective instruments.

In accordance with yet another embodiment, a method is provided for preparing for a surgical procedure that includes identifying a plurality of surgical instruments to be included in a set for the surgical procedure; and adding an identifier member on a shaft or handpiece of each surgical instrument, the identifier member identifying one of a type and a class of an end effector on the respective instrument.

In accordance with another embodiment, a surgical instrument is provided that includes a shaft including a proximal end and a distal end sized for introduction into a patient's body; a tool tip on the distal end including an end effector; a handpiece or connector for coupling to a robotic control system on the proximal end; and an identifier feature on one of the shaft and handpiece configured to identify one of a type and a class of the end effector.

In one embodiment, the identifier feature comprises a rotating knob on the handpiece, the knob comprising an outer surface having a predetermined geometric shape corresponding to the type or class of the end effector. In another embodiment, the identifier feature comprises a geometric outer surface extending along a portion of the shaft, the outer surface having a predetermined geometric shape corresponding to the type or class of the end effector. In yet another embodiment, the identifier feature comprises a light source, e.g., a light-emitting diode, luminescent material, and the like, configured to emit a predetermined color to identify one of a type and a class of the end effector.

In accordance with still another embodiment, a system is provided for performing a surgical procedure that includes a plurality of surgical instruments, each instrument comprising a shaft including a proximal end and a distal end sized for introduction into a patient's body, a tool tip on the distal end including an end effector, and a handpiece or connector on the proximal end; and identifier features on one of the shaft and the handpiece of the surgical instruments configured to identify one of a type and a class of the end effectors on the respective instruments.

In accordance with yet another embodiment, a system is provided for performing a surgical procedure that includes a plurality of surgical instruments, each instrument comprising a shaft including a proximal end and a distal end sized for introduction into a patient's body, a tool tip on the distal end including an end effector, and a handpiece or connector on the proximal end; and identifier features on one of the shaft and the handpiece or connector of the surgical instruments configured to emit colored light to identify one of a type and a class of the end effectors on the respective instruments.

In accordance with still another embodiment, a method is provided for performing a laparoscopic procedure within a patient's body that includes introducing a tool tip on a distal end of a surgical instrument into a surgical space within the patient's body; and observing a light-emitting identifier feature on one of the tool tip and the distal end of the surgical instrument within the surgical space to identify the type of tool tip.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

FIG. 1 is a side view of an exemplary embodiment of a conventional MIS instrument including a handle, shaft, and working tip.

FIGS. 2A and 2B are details of exemplary embodiments of conventional MIS instrument tool tips, e.g., a curved scissor tip (FIG. 2A) and a curved dissector tip (FIG. 2B) demonstrating their similar appearance and the potential for mis-identification.

DETAILED DESCRIPTION OF THE EXEMPLARY EMBODIMENTS

Figures 3A, 3B, 3C, 3D, 3E, 3F:
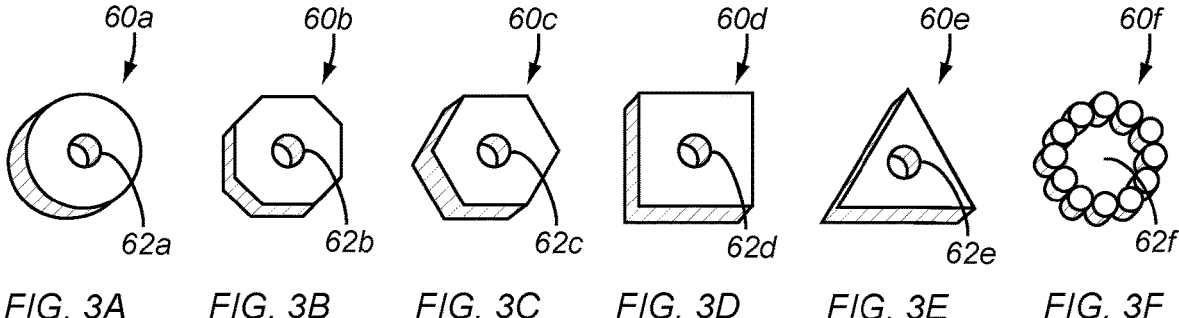
FIGS. 3A-3F show exemplary embodiments of add-on identifier knobs that are suitable for aftermarket modification of MIS instruments, such as the instrument shown in FIG. 1.

Turning to the drawings, FIG. 1 shows an exemplary embodiment of a typical MIS instrument 10 including a shaft 20 having a handpiece 30 on its proximal end 22 and a tool tip 40 on its distal end 24. The handpiece 30 generally includes a body 32 at least partially fixed relative to the shaft 20, a handgrip 34 movable relative to the body 32, and a locking mechanism 36. The shaft 20 may be rotatable relative to the handpiece 30, e.g., with the body 32 irremovable but rotatable relative to the proximal end 22 of the shaft. In this case, a knob 38 may be provided to enable a surgeon or other user to rotate the shaft 20 relative to the handpiece 30. For example, the knob 38 and handpiece 30 may include mating knurls or other features, which may be separable to allow rotation of the shaft 20 yet biased to engage to secure the shaft 20 in a set orientation relative to the handpiece 30.

Alternatively, for robotic surgical procedures, one or more connectors (not shown) may be provided instead of the handpiece 30 on the instrument 10 (or any other embodiments herein). Such connector(s) may be used to couple the proximal end 22 of the shaft 20 to a robotic control system (not shown). A console may be used to manipulate the shaft 20 and/or tool tip 40 remotely during such a procedure.

The tool tip 40 may have a generally low profile, e.g., not substantially larger than the outer dimension of the shaft 20 (e.g., when elements 42 of the tool tip 40 are closed), which may facilitate introduction of the tool tip 40 through a trocar or other port (not shown) into a surgical space. The tool tip 40 may include one of a variety of end effectors, for example, a pair of scissors (e.g., as shown in FIG. 2A), a dissector (e.g., as shown in FIG. 2B), a set of forceps, a grasper, a coagulator, and the like (not shown). The tool tip 40 may be substantially permanently attached to the distal end 24 of the shaft 20 such that the entire instrument 10 is integrally inseparable. Alternatively, the tool tip 40 may be removable and/or replaceable, e.g., such that the tool tip 40 may be exchanged for one or more different end effectors, during a procedure and/or between procedures. For example, a shaft 20 and handpiece 30 may be provided that are integral with one another, with the shaft 20 including one or more connectors (not shown) on the distal end 24 for coupling a tool tip 40 to the shaft 20 (which may include one or more corresponding mating connectors, also not shown).

The tool tip 40 may include one or more actuatable elements, which may be activated or manipulated from the handpiece 30. For example, as shown in FIG. 1, the tool tip 40 includes a pair of scissors with at least one of the blade elements 42 of the scissors being movable to open and close. For example, one element 42 may be substantially fixed relative to the shaft 20 and the other element 42 may be coupled to the handgrip 34, e.g., by an actuator shaft or member (not shown) extending through the shaft 20. Thus, the elements 42 may be moved between closed and open positions using the handgrip 34. The handgrip 34 may be pivotally coupled to the body 32 of the handpiece 30, e.g., to allow a user to pull and release or otherwise actuate the elements 42 of the tool tip 40. In an exemplary embodiment, the handgrip 34 and/or tool tip 40 may be biased to the closed position with the handgrip 34 moving the elements 42 to the open position against the bias, or the handgrip 34 may be lockable but movable between first and second positions to open and close the elements 42.

In addition, the handpiece 30 may include a locking mechanism 36, e.g., a locking switch, which may be moved between locked (inactive) and unlocked (active) positions. For example, with the locking mechanism 36 engaged, the elements 42 on the tool tip 40 be locked closed to prevent accidental opening of the elements 42 (locking the handgrip 34 and/or disengaging the handgrip 34 from the tool tip 40), e.g., during handling outside the patient's body, during introduction, and/or during manipulation of tissues in the surgical space. Once the tool tip 40 is positioned within a surgical space, the locking mechanism 36 may be unlocked, thereby allowing the handgrip 34 to be manipulated to open and close or otherwise actuate the tool tip 40. The locking mechanism 36 may then be re-locked at any time, e.g., to grasp tissues during the procedure and/or to facilitate removal.

FIGS. 2A and 2B show details of two exemplary tool tips 40a, 40b that have similar sizes, shapes and configurations yet dissimilar functions. The tool tip 40a of FIG. 2A is a curved pair of scissors with cutting elements 42a having sharpened edges and, optionally sharpened tips, while the tool tip 40b of FIG. 2B is a curved dissector tip with blunt elements 42b without sharp edges or tips. It should be apparent that, given the similar appearance, e.g., size, shape, and/or profile, of the two tool tips 40a, 40b, there is substantially risk of mis-identification or confusion between two instruments including the tool tips 40a, 40b during a procedure, particularly in a darkened operating room, with the potential for serious harm to the patient and/or user.

FIGS. 3A-3F show exemplary embodiments of add-on devices, e.g., identifier knobs 60a-60f, which may be added to specific types instruments to facilitate identification. Generally, the identifier knobs 60a-60F include annular or partially annular bodies including holes or apertures 62a-62f sized to be placed over the shafts of individual of instruments, and including outer peripheries or shapes to facilitate distinguishing different instruments, e.g., round (FIG. 3A), octagonal (FIG. 3B), hexagonal (FIG. 3C), square (FIG. 3D), triangular (FIG. 3E), or multi-lobulated (FIG. 3F) outer surface shapes.

In addition or alternatively, each identifier knob 60a-60f may have a corresponding color to distinguish different instruments to which each identifier knobs 60a-60f is added. For example, the entire identifier knobs 60a-60f may be formed material having corresponding colors. Alternatively, only a portion of each identifier knob may include a corresponding color, e.g., a colored stripe, a colored alphanumeric symbol (e.g., one or more words, letters, numbers, and/or combinations thereof), a colored surface, a colored picture (e.g., showing an enlarged tool tip), and the like. In addition or alternatively, the color may be luminescent, e.g., such that at least a portion of the identifier knob emits light, to allow the color and/or other feature(s) to be seen in a darkened operating room. In a further alternative, the color may be highly reflective such that the identifier knob readily reflects light to enhance identifying the color under low light conditions. The colors may correspond to predetermined subsets of "classes" of tools, e.g., red for "sharp" tools and green "blunt" tools, or different individual types of tool tips, such as those identified elsewhere herein.

The identifier knobs 60a-60f may be constructed of moderately pliable and/or sterilizable synthetic material, e.g., plastic, and the like, with specific shapes and appropriately-sized central holes or apertures 62a-62f to facilitate installation on a set of instruments, e.g., before a procedure. For example, with reference to FIG. 4, the material of the identifier knob 60 may be elastically stretched partially when the identifier knob 60 is inserted over a tool tip 40 onto the shaft 20 of an instrument 10,' with the material biased to frictionally engage the shaft 20. Alternatively, the material of a "C" or partially annular shaped identifier knob (not shown) may be separated or opened to allow the shaft 20 to be received within the aperture, whereupon the identifier knob may be released to engage around the shaft 20.

Figure 4:
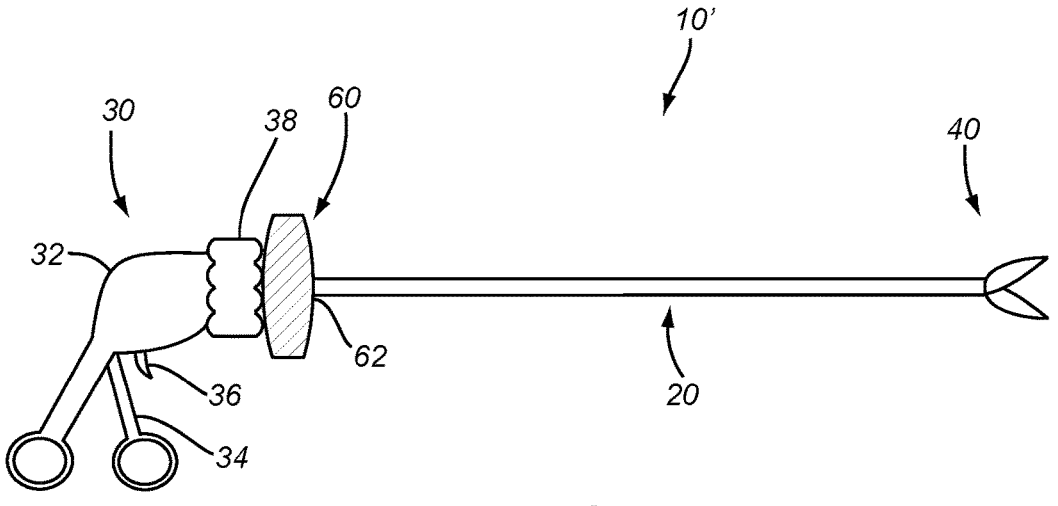
FIG. 4 is a side view of an exemplary MIS instrument including an identifier knob, such as any of the knobs of FIGS. 3A-3F, attached over the shaft adjacent the handle.
Figures 5A, 5B, 5C, 5D, 5E:
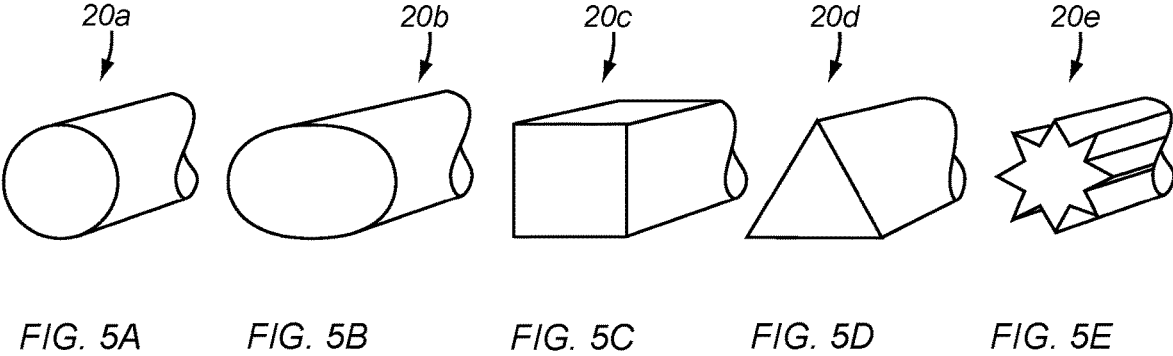
FIG. 5A-5E are cross-sectional views of exemplary embodiments of shaft shapes that may be provided for instrument shafts to provide tactile and/or visual indicators facilitating distinguishing instruments from one another.

As shown in FIG. 4, the hole or aperture 62 of the identifier knob 60 may be sized to engage the shaft 20 of an instrument 10,' for example, simply by friction fit, to allow removal upon completing a procedure (particularly where the instruments are to be sterilized or otherwise prepared for a future procedure). Alternatively, the identifier knobs 60a-60f may include one or more detents or other connectors (not shown), e.g., which may be received over or otherwise engaged with the existing knob 38 on the handpiece 30 to secure the identifier knobs 60a-60f onto a desired instrument. The connector(s) may be separable, e.g., to allow the identifier knobs to be removed from a set of instruments, e.g., after a procedure. Alternatively, the connector(s) may be inseparable from the existing knob 38 and/or other structure of the instrument 10,' e.g., if the material of the identifier knob 60 is capable of being sterilized or otherwise treated with the instrument 10' between procedures, or if the instrument 10' is single-use and intended to be discarded after completing an individual procedure. Thus, the identifier knob 60 may become a permanent addition to the instrument 10' to facilitate identification during multiple future procedures.

A different-shaped identifier knob 60 may be added to each instrument 10' in a set or kit (only a single instrument 10' is shown in FIG. 4 for simplicity), which is assembled or otherwise organized for a particular procedure. For example, a schedule or menu may be provided to medical personnel assembling a kit to indicate which specific identifier knob to add to each instrument in the set or kit, e.g., based on the tool type or their function, thereby uniquely identifying each instrument in the set or kit. Alternatively, a different shaped knob may be added to instruments of different classes (e.g., the same or similar-shaped knobs added to "sharp" instruments and different knobs added to "blunt" instruments, as described elsewhere herein). In this alternative, the sharp identifier knobs may warn the user to use additional care when handling an instrument in the "sharp" or other class, which may have increased risk to the patient and/or user.

With additional reference to FIG. 4, with an identifier knob 60 placed adjacent the existing knob 38, a surgeon or other user may be able to easily touch the identifier knob 60, e.g., with the surgeon's index finger or otherwise, before introducing the tool tip 40 into a trocar or otherwise into a patient's body (not shown) or after such introduction. Thus, the identifier knob 60 may provide tactile (in addition to visual) confirmation to the surgeon of the type of instrument 10' in use, which may provide increased safety and/or efficiency (e.g., reducing the chance that the surgeon erroneously introduces the wrong instrument into a surgical space and has to remove or exchange the instrument). Such a standardized system may be recognized intuitively and universally by surgeons and medical personnel to identify instruments by their functions.

The instrument shown in FIG. 4 may be part of a kit or set of instruments that may be assembled in preparation for a surgical procedure. In an exemplary method, in preparing for a surgical procedure, a plurality of surgical instruments (each of which may be similar to the instrument 10' shown in FIG. 4, although including different tool tips than the tool tip 40) may be identified and/or selected to be included in a set for the surgical procedure. An identifier member, e.g., an identifier knob 60, may be added on the shaft 20 or handpiece 30 of each surgical instrument 10', e.g., to identify one of a type and a class of the element(s) 42 of the tool tip 40 on the respective instrument 10'. Optionally, a schedule or menu may be provided with the kit or set, e.g., identifying each type or class of instrument and the shape and/or other features of the identified by the corresponding identifier knob 60.

After the procedure is completed, the identifier knobs 60 may be removed from the instruments, and the instruments may be sterilized and/or otherwise prepared for a future procedure. The identifier knobs 60 may then be discarded (e.g., if the identifier knobs 60 are constructed to be single-use) or, optionally, may be sterilized and/or otherwise prepared so that they may be added to another set or kit of instruments for a future procedure. Alternatively, the identifier knobs 60 may remain indefinitely on the instruments for identification during future procedures.

Turning to FIGS. 5A-5E, exemplary embodiments of geometric profiles of instrument shafts 20a-20e are shown, which may be provided on different instruments (not shown), such as that shown in FIG. 1. For example, during manufacturing, different types (or different classes) of instruments may have different shaft geometries, which may facilitate distinguishing and/or identification of specific types of MIS instruments. For example, circular shafts 20a, such as that shown in FIG. 5A, may be provided for conventional instruments, such as that shown in FIG. 1. Instead of such circular shafts, individual types or classes of instruments may have other cross-sectional or outer surface shapes, e.g., elliptical 20b (FIG. 5B), square 20c (FIG. 5C), triangular 20d (FIG. 5D), star-shaped 20e (FIG. 5E), and the like.

The distinguishing shapes may be provided on the entire length of the shafts, or only on one or more portions thereof (e.g., along a predetermined length extending distally from the handpiece, proximally from the tool tip, and the like). Thus, rather than placing add-on features on instruments, the instruments (such as any of those described elsewhere herein) may be manufactured from shafts 20a-20e having different outer cross-sectional shapes, which may correspond to individual types or classes of instruments. Such shapes may again provide a tactile and/or visual indication of the type or class of the tool tip on the selected instrument. Such tactile differences may be particularly useful in laparoscopic procedures, which may be performed in darkened operating rooms, reducing the ability to visually distinguish instruments, particularly based solely on attempting to observe the tool tips.

Figure 6:
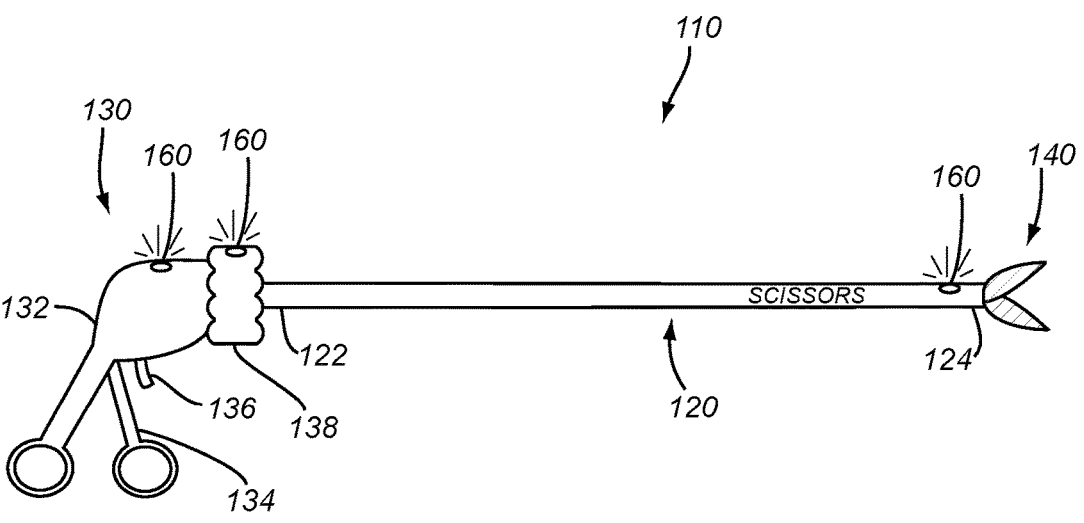
FIG. 6 is a side view an exemplary embodiment of a MIS instrument including one or more features to identify and/or distinguish the instrument from other instruments.

Turning to FIG. 6, another exemplary embodiment of a surgical instrument 110 is shown, which may generally include similar features to the instrument 10 of FIG. 1, except that the instrument 110 includes one or more identifier features 160 (instead of an identifier knob 60). For example, the instrument 110 may generally include a shaft 120 having a handpiece 130 on its proximal end 122 and a tool tip 140 on its distal end 124. The handpiece 130 generally includes a body 132 at least partially fixed relative to the shaft 120, a handgrip 134 movable relative to the body 132 to actuate the tool tip 140, a locking mechanism 136, and a rotating knob 138, similar to other embodiments herein. Alternatively, one or more connectors (not shown) may be provided on the proximal end 122 of the shaft 120 instead of the handpiece 130, e.g., for use with robotic surgical systems.

The identifier features 160 may be provided at one or more locations on the instrument 110, e.g., on the handpiece 130, as indicated by identifier feature 160A, on the knob 138, as indicated by identifier feature 160B, on the proximal end 122 of the shaft 120 (not shown), and/or on the distal end 124 of the shaft 120 or the tool tip 140 itself, as indicated by identifier feature 160C. In one embodiment, an identifier feature may be provided at 160A or 160B to allow a surgeon and/or other medical staff to identify a class or type of the tool tip 140 provided on the instrument 110. Such feature(s) 160A, 160B may facilitate identification of the tool tip 140 while the instrument 110 is on a tool tray or being handled outside a patient's body as well as when the shaft 120 and tool tip 140 have been inserted into a trocar or port (not shown) during a procedure.

In addition or alternatively, an identifier feature 160C may be provided to facilitate identification of the tool tip 140 when the tool tip 140 is being observed during a procedure. For example, during a laparoscopic, robotic, or other MIS procedure, the surgeon may observe the surgical space using a laparoscope or other instrument positioned through a trocar or port into the surgical space. The identifier feature 160C may be visible within the surgical space, which may facilitate the surgeon confirming that the correct instrument has been selected and introduced into the surgical space. Such a distal identifier feature 160C may be particularly useful for robotic surgical procedures since the surgeon may not be in the operating room with the patient and may not be able to inspect the proximal end 122 of the instrument 110.

In an exemplary embodiment, the identifier feature(s) 160 may include one or more colored light sources, e.g., light-emitting diodes, with different colors used to identify the type or class of the tool tip of each instrument. In this embodiment, a power source, e.g., a battery or cord for connecting to an external energy source (not shown), may be provided, e.g., on or in the handpiece 130.

Such a light source may facilitate identifying the tool tip when a procedure is being performed in a darkened operating room. Alternatively, the identifier feature(s) 160 may include luminescent material applied to a desired surface, which may include different colors. In this alternative, no power source may be needed, as the luminescent material may automatically emit light, e.g., after being exposed to a light source for a predetermined time or due to a chemical or biological reaction.

In yet another alternative, one or more alphanumeric terms (e.g., words, letters, and/or numbers), symbols, and the like may be provided identifying the class or type of the tool tip of each instrument, e.g., "SCISSORS" as shown on the shaft 120 of the instrument in FIG. 6. Such terms and symbols may engrossed on the shaft 120, the handpiece 130, and/or elsewhere on the instrument 110, and may include corresponding colors (luminescent or not) and/or other features to identify the type or class of tool tip for each instrument.

The identifier feature(s) may correspond to an accepted convention and/or may be identified in a list or schedule provided with a set of instruments, similar to the identifier knobs described elsewhere herein. In addition or alternatively, the rotating knob 138 itself may have a predetermined shape and/or color, similar to the identifier knobs described elsewhere herein, to identify the tool tip.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for performing a laparoscopic procedure within a patient's body, comprising:
   introducing a tool tip on a distal end of a surgical instrument into a surgical space within the patient's body;
   introducing a laparoscope through a trocar or port into the surgical space; and
   after introducing the laparoscope, while the tool tip is in the surgical space, observing a light-emitting identifier feature on one of the tool tip and the distal end of the surgical instrument through the laparoscope to identify the type of tool tip.

2. The method of claim 1, wherein observing a light-emitting identifier feature comprises:
   identifying that the surgical instrument has the wrong type of tool tip;
   removing the surgical instrument from the surgical space;
   introducing a tool tip of a second surgical instrument into the surgical space; and
   using the tool tip of the second surgical instrument to perform one or more steps of the laparoscopic procedure.

3. A method for performing a laparoscopic procedure within a patient's body, comprising:
   adding a removable light-emitting identifier feature on a proximal end of a surgical instrument before the procedure;
   introducing a tool tip on a distal end of the surgical instrument into a surgical space within the patient's body; and
   while the tool tip is in the surgical space, observing the light-emitting identifier feature on the surgical instrument to identify the type of tool tip.

4. The method of claim 3, further comprising observing the identifier feature to facilitate identification of the tool tip while the instrument is on a tool tray or being handled outside the patient's body.

5. The method of claim 3, wherein the identifier feature comprises a light-emitting diode.

6. The method of claim 3, wherein the identifier feature comprises luminescent material.

7. The method of claim 3, wherein the tool tip is introduced into the surgical space during a robotic surgical procedure.

8. The method of claim 7, wherein the tool tip is introduced robotically by a surgeon using a robotic surgical console.

9. The method of claim 3, further comprising using the tool tip to perform one or more steps of the laparoscopic procedure.

10. A method for performing a laparoscopic procedure within a patient's body, comprising:

providing a set of surgical instruments, each instrument comprising a shaft including a proximal end and a distal end sized for introduction into a patient's body, a tool tip on the distal end including an end effector, a handpiece on the proximal end;

adding a removable light-emitting identifier feature to each of the surgical instruments before the procedure to identify one of a type and a class of the end effector of each of the surgical instruments;

introducing a tool tip of a first instrument into a surgical space within the patient's body; and while the tool tip is in the surgical space, observing the identifier feature on the first instrument to identify the type of tool tip to identify one of a type and a class of the end effector on the first instrument.

11. The method of claim 10, wherein the surgical instruments of the set include end effectors selected from two or more of a pair of scissors, a dissector, a set of forceps, a grasper, a needle holder, and a coagulator.

12. The method of claim 10, wherein the identifier members have different colors for each of a pair of scissors, a dissector, a set of forceps, a grasper, a needle holder, and a coagulator.

13. The method of claim 10, wherein, after observing the identifier member on the first instrument, the method further comprises:

identifying that the first instrument has the wrong type of tool tip;

removing the first instrument from the surgical space;

introducing a tool tip of a second instrument into the surgical space; and using the tool tip of the second instrument to perform one or more steps of the laparoscopic procedure.

14. The method of claim 10, wherein each of the identifier features comprises a light-emitting diode.

15. The method of claim 10, wherein each of the identifier features comprises luminescent material.

16. The method of claim 10, further comprising introducing a tool tip of a second instrument into a surgical space within the patient's body; and while the tool tip is in the surgical space, observing the identifier member of the second instrument to identify one of a type and a class of the end effector on the first instrument or to distinguish the first instrument from the second instrument.

17. The method of claim 10, wherein the identifier feature is provided on one of the handpiece, the proximal end of each surgical instrument, and a knob on the proximal end of each surgical instrument, wherein the identifier feature has a predetermined geometric cross-sectional shape configured to provide tactile confirmation of one of the type and the class of the end effector on the respective surgical instrument.

18. The method of claim 10, wherein the light-emitting identifier feature is added on a proximal end of each of the surgical instruments.

19. The method of claim 10, further comprising removing the light-emitting identifier feature from each of the surgical instruments after the procedure.

20. The method of claim 3, wherein the light-emitting identifier feature is added to one of a handpiece and a knob of the surgical instrument before introducing the distal tip into the surgical space.

21. The method of claim 20, further comprising removing the light-emitting identifier feature from the surgical instrument after the procedure.

22. The method of claim 3, wherein adding the removable light-emitting identifier feature comprises attaching the removable light-emitting identifier feature over the proximal end of the shaft adjacent a handle.

23. The method of claim 10, wherein adding the removable light-emitting identifier feature comprises adding the light-emitting identifier feature to one of a handpiece and a knob of each of the surgical instruments.

24. The method of claim 10, wherein adding the removable light-emitting identifier feature comprises attaching the removable light-emitting identifier feature over the proximal end of the shaft adjacent a handle of each of the surgical instruments.

25. The method of claim 1, wherein the tool tip is introduced into the surgical space during a robotic surgical procedure, and wherein the surgeon observes the light-emitting identifier from a console.

* * * * *